(12) United States Patent
Tankovich et al.

(10) Patent No.: US 6,569,156 B1
(45) Date of Patent: May 27, 2003

(54) MEDICAL COSMETIC LASER WITH SECOND WAVELENGTH ENHANCEMENT

(76) Inventors: Nikolai Tankovich, 9361 Stargaze Ave., San Diego, CA (US) 92129; Alexei Lukashev, 3574 Caminito El Riacon, #97, San Diego, CA (US) 92130

( * ) Notice: Subject to any disclaimer, the term of this patent is extended or adjusted under 35 U.S.C. 154(b) by 0 days.

(21) Appl. No.: 09/664,463

(22) Filed: Sep. 18, 2000

Related U.S. Application Data

(63) Continuation-in-part of application No. 09/608,020, filed on Jun. 30, 2000.

(51) Int. Cl.$^7$ ............................................. A61L 18/20
(52) U.S. Cl. ............................ 606/10; 606/3; 606/13
(58) Field of Search ............................. 606/3, 9–13

(56) References Cited

U.S. PATENT DOCUMENTS

| | | | | |
|---|---|---|---|---|
| 4,580,557 A | * | 4/1986 | Hertzmann | 606/12 |
| 4,672,969 A | * | 6/1987 | Dew | 606/3 |
| 4,852,567 A | * | 8/1989 | Sinofsky | 606/3 |
| 4,917,084 A | * | 4/1990 | Sinofsky | 606/3 |
| 5,312,396 A | * | 5/1994 | Feld et al. | 606/11 |

* cited by examiner

*Primary Examiner*—David M. Shay
(74) *Attorney, Agent, or Firm*—John R. Ross; John R. Ross, III

(57) ABSTRACT

A laser system and process by which prior art medical and cosmetic laser techniques using laser beams chosen to produce selective thermolysis are enhanced by the addition of a second laser beam chosen for much deeper transmission in tissue and more uniform absorption. Preferred embodiments include enforcement with a 1079 nm YAP:Nd laser beam of a 532 nm beam produced by a frequency doubled YAG:Nd laser beam.

12 Claims, 4 Drawing Sheets

Absorption coefficient
of oxy- and deoxygenated blood at HCT = 5%

Absorption spectra of the skin chromophores
and the Caucasian type of skin though this laser light works well on small veins it does not perform so well on larger veins mainly because of high absorption of oxyhemoglobin in upper part of a vein. This creates a shield which prevents laser light from penetrating deeper to the lower part of the vein. As a result larger veins are coagulated non-uniformly and vein destruction of the larger veins is not satisfactory.

MEDICAL COSMETIC LASER WITH SECOND WAVELENGTH ENHANCEMENT

This invention relates to laser systems and in particular to multi-wavelength laser systems. This Application is a CIP of Ser. No. 09/608,020 filed Jun. 30, 2000.

BACKGROUND OF THE INVENTION

Use of lasers for medical purposes is well established. Lasers are used extensively for cosmetic purposes such as hair removal, vein treatment, skin rejuvenation, treatment of telangeatesia and treatment of port wine stain. Each of these treatments is preferably performed with a laser producing laser pulses at a wavelength chosen to be most effective for the particular treatment. Some wavelengths are very preferentially absorbed in a particular type of tissue. Some wavelengths are highly absorbed in skin tissue with penetration depths of only a few microns. Other wavelengths have absorption coefficients substantially less than 1/cm and penetrate substantial depths in skin and other tissue. FIGS. 6 and 7 show absorption coefficients as a function of wavelengths for blood, human skin and melanin. A Nd:YAG laser operating at 1320 nm (with high absorption in skin tissue) may be used for skin rejuvenation and micro skin surgery. Treatment of port wine stains is usually performed using a dye laser operating at a wavelength of 577 nm where the absorption in blood is high. Another example is the 532 nm wavelength of frequency doubled YAG:Nd laser is widely used to treat vascular lesions like telangiectasia, or small facial veins. Though this laser light works well on small veins it does not perform so well on larger veins mainly because of high absorption of oxyhemoglobin in upper part of a vein. This creates a shield which prevents laser light from penetrating deeper to the lower part of the vein. As a result larger veins are coagulated non-uniformly and vein destruction of the larger veins is not satisfactory.

Use of a laser beam matched to a peak or relatively high absorption in tissue to treat the tissue is referred to as "selective thermolysis". When wavelengths which penetrate deeply and are absorbed relatively uniformly in tissue are used to treat the tissue, the treatment is referred to as "non-selective thermolysis".

What is needed are enhancement of the selective thermolysis lasers and methods to improve results of medical and cosmetic treatment.

SUMMARY OF THE INVENTION

The present invention provides a laser system and process by which prior art medical and cosmetic laser techniques using laser beams chosen to produce selective thermolysis are enhanced by the addition of a second laser beam chosen for much deeper transmission in tissue and more uniform absorption. Preferred embodiments include enforcement with a 1079 nm YAP:Nd laser beam of a 532 nm beam produced by a frequency doubled YAG:Nd laser beam.

DETAILED DESCRIPTION OF PREFERRED EMBODIMENTS

Preferred embodiments of the present invention may be described by reference to the drawings.

First Preferred Embodiment

1079 nm Enhancement of Frequency Doubled YAG:Nd 532 nm KTP Beam

A well known technique for selective thermolysis of blood vessels involves the use 532 nm KTP laser (which is basically Nd:YAG laser with second harmonics generation in KTP crystal) to produce high absorption of green light in oxihemoglobin which leads to the selective thermolysis of blood vessels.

Figure 1:
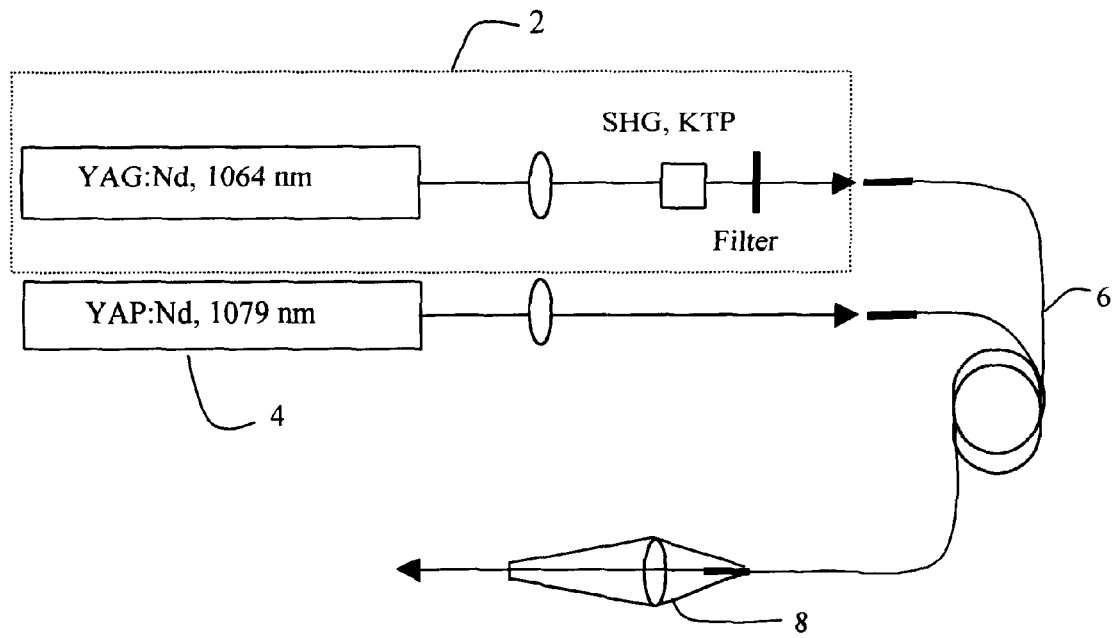
FIG. 1 is a drawing showing the principal features of a preferred embodiment of the present invention for enhancing a KTP laser

A first preferred embodiment can be described by reference to FIG. 1. A prior art KTP laser system is depicted at 2. Its output at 532 nm is combined with the output of a YAP:Nd, 1079 nm laser 4 using an beam combining optical fiber 6 connected to hand piece 8.

The YAP:Nd laser at 1079 nm is used to improve selective thermolysis at 532 nm by using non-selective thermolysis at 1079 nm. The 1079 nm laser light of YAP:Nd laser has no specific absorption in blood vessels. The 1079 nm light is very highly scattered in skin and is fairly uniformly absorbed down to depths of a few millimeters. The 1079 nm light thus heats the large blood vessel from the sides and from the bottom as well as tissue around it. This enhanced heating when added to the heating produced in the large vessels by the 532 nm light produces much better destruction of the larger blood vessels as compared to the destruction produced by the 532 nm beam alone. Persons skilled in this art will recognize that the 1079 nm beam heats skin tissue surrounding the blood vessel about the same extent as the blood and the blood vessel. Therefore care must be taken to be certain that excessive destruction of the surrounding skin tissue does not occur. Tissue destruction generally depends on temperature and time. A good discussion of this temperature-time relationship to tissue destruction is provided in *Phase Transformation and Ablation in Laser Treated Solids* by Emil Solol published by John Wiley and Sons and is available at Amazon.com and at major bookstores. Therefore, care should be taken to apply the laser energy at rates will produce only minimal damage to tissue which is not targeted. A good technique to keep the temperature of non-targeted tissue below the damage threshold is to cool the skin surface before, during and after the laser treatment. A preferred skin cooling technique is described in U.S. Pat. No. 6,059,820 which is incorporated herein by reference. A preferred technique is to apply the two beams in bursts of short pulses with about 10 pulses in two seconds so that the total energy deposited in the skin is about 40 Joules/cm2 if surface cooling is not used. With surface cooling the energy deposited could be increased to about 70 Joules/cm2. Preferably, the ratio of the 1079 nm energy to the 532 nm energy should be in the range of about 1 to 2.

Components

Green 532 nm optical laser deck (which includes the laser optics, the gain medium and the pumping source) is available from HGM Corporation with office in Salt Lake City, Utah. Other models of KTP optical laser deck are available from Viridis by Quantel, Les Ulis, France, VersaPulse by Coherent, Santa Clara, Calif., Iriderm DioLite 532 by Iridex, Mountain View, Calif., Aura KTP/532 by Laserscope, San Jose, Calif. Optical fiber with two inputs and one output is available from Newport Corporation, Irvine, Calif. The YAP:Nd laser is available from Fotona d.d. with offices in Ljubljana, Slovenia.

Other Similar Embodiments

Dye laser in green yellow range 550–585 nm might be also improved by using YAP:Nd as a second preferred embodiment. Dye laser deck might be Photogenica by Synosure with office in Chelmsford, Mass.

Second Preferred Embodiment

YAP Enhancer for Alexandrite Laser

A well known technique for hair removal and for treating pigmented lesions on the skin involves the use of Alexandrite lasers at 755 nm which utilizes an Alexandrite crystal as the gain medium. This technique is based on the fact that 755 nm laser light is absorbed by melanin in skin and hair that leads to coagulation of those tissues. However, light at this wavelength does not penetrate skin tissue very well and as a result it is difficult to target the hair up to the very root without seriously damaging the non-targeted skin tissue. Also this type of laser is difficult to use for hair removal on dark type of skin because of higher risk to damage skin.

Figure 2:
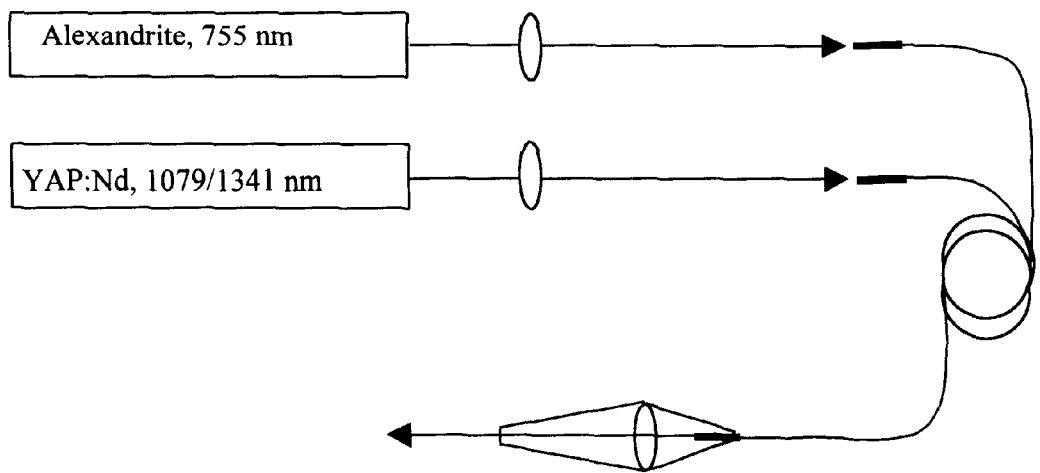
FIG. 2 is a drawing showing the enhancement of an Alexandrite laser.

FIG. 2 describes a second preferred embodiment in which the prior art Alexandrite laser beam is enhanced with the output of a YAP:Nd, 1079 nm laser. The YAP:Nd 1079 nm laser does not have specific high absorption in skin and the laser light penetrates much deeper in skin than Alexandrite 755 nm. With the help of 1079 nm light it is easy to provide sufficient energy deposition at deeper layers of skin where hair papilla and stem cells for new hair growth are located. This combination increases the damage to the hair roots to provide permanent hair removal or to extend the period for the new hair to appear.

Optical deck for Alexandrite laser is available from Cynosure Corporation, Chelmsford, Mass. The laser can also be obtained from Candela Corporation with office in Wayland, Mass.

Third Preferred Embodiment

YAP Enhancer for Diode Laser

Figure 3:
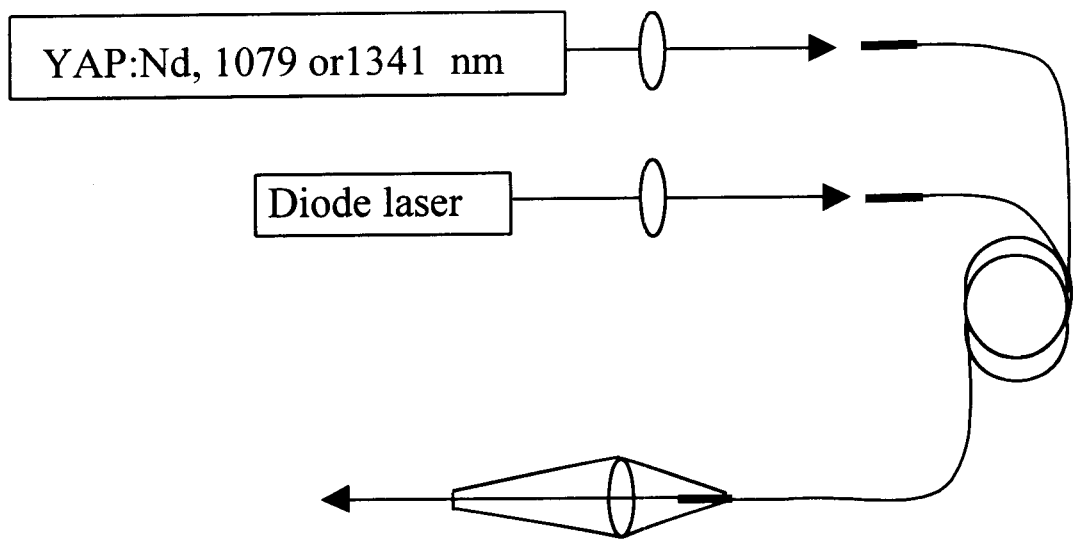
FIGS. 3 and 4 are drawings showing the enhancement of diode lasers.

As shown in FIG. 3 YAP laser can be used to enhance performance of diode lasers using the same approach as described above. Medical laser diode laser might be available from Coherent, Santa Clara, Calif., model LightSheer, DioMed, Boston, Mass., Both lasers operate at 800–810 nm range and might be improved by both 1079 and 1341 nm YAP:Nd laser. 1079 nm wavelength of YAP:Nd laser improves hair removal using diodes lasers, while 1340 nm line of YAP:Nd improves coagulation of small blood vessel by non-selective thermolysis.

All variety of laser diodes in wavelength range 650–1550 are available from SLI Corporation Binghamton, N.Y. YAP laser might be located at the same platform as the diode laser. Optical fiber with two inputs and one output is available from Newport Cortoration, Irvine, Calif.

Figure 4:
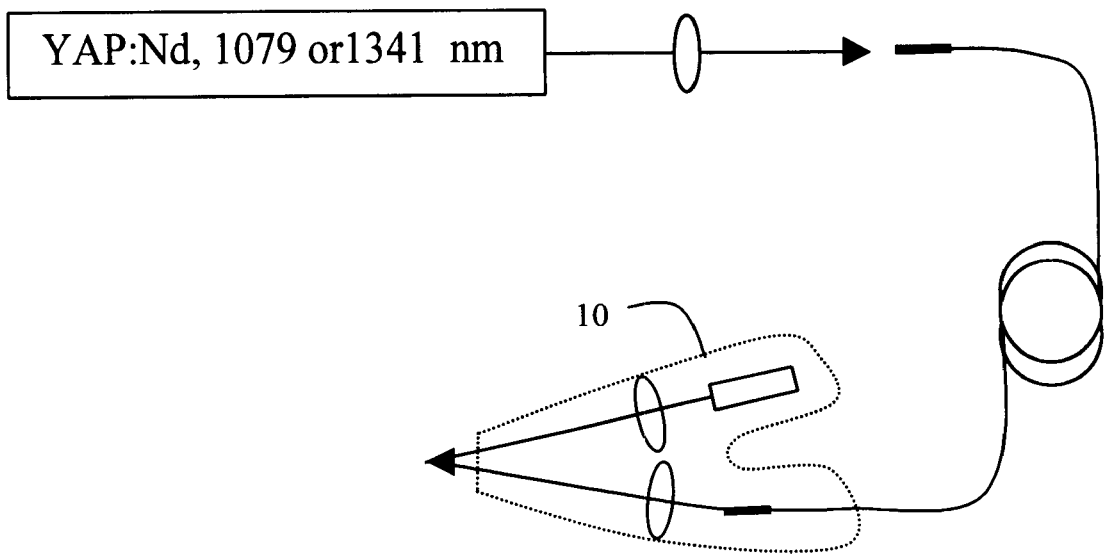

In the other preferred embodiment laser diode might be placed in the handpiece as shown at 10 in FIG. 4.

Fourth Preferred Embodiment

Figure 5:
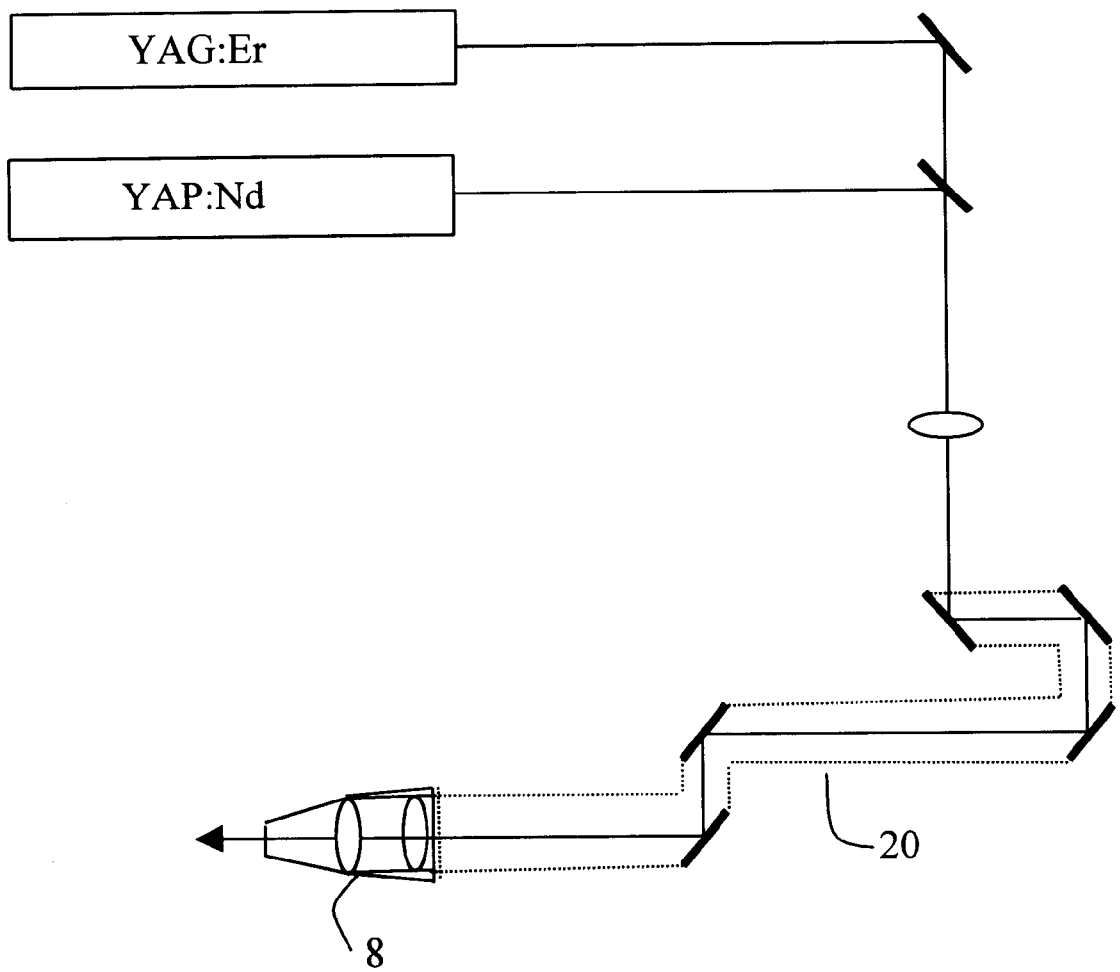
FIG. 5 is a drawing showing the enhancement of an Er laser.
Figure 6:
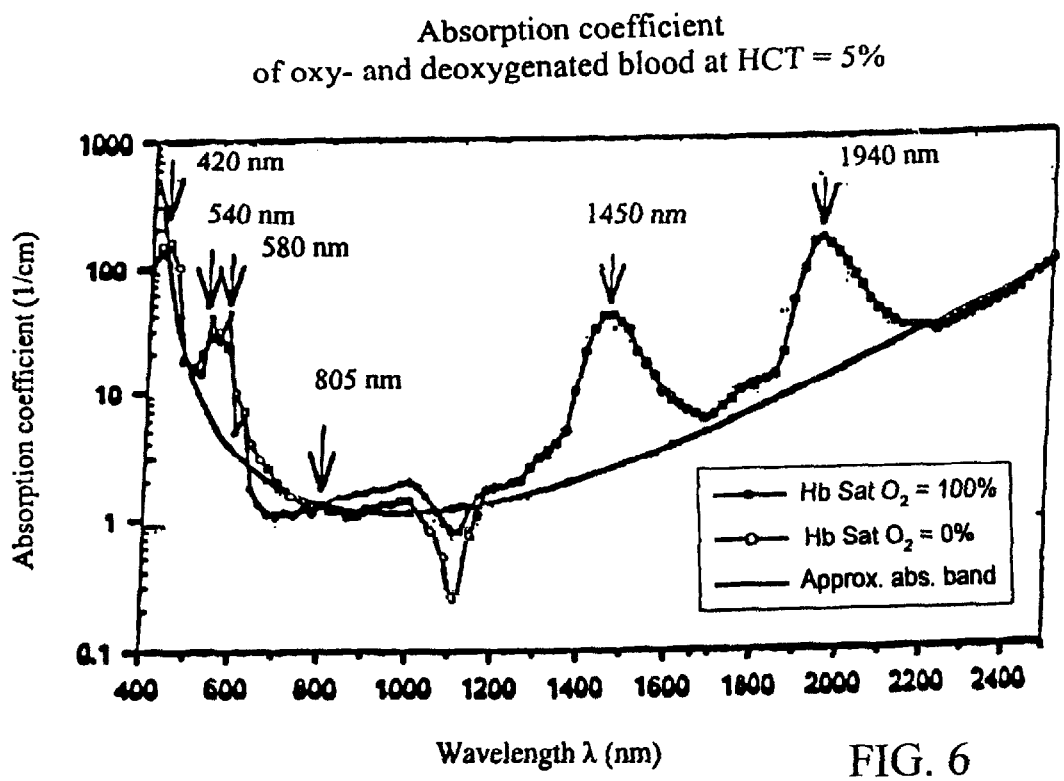
FIGS. 6 and 7 show absorption coefficient as a function of wavelength for selected tissue and blood.
Figure 7:
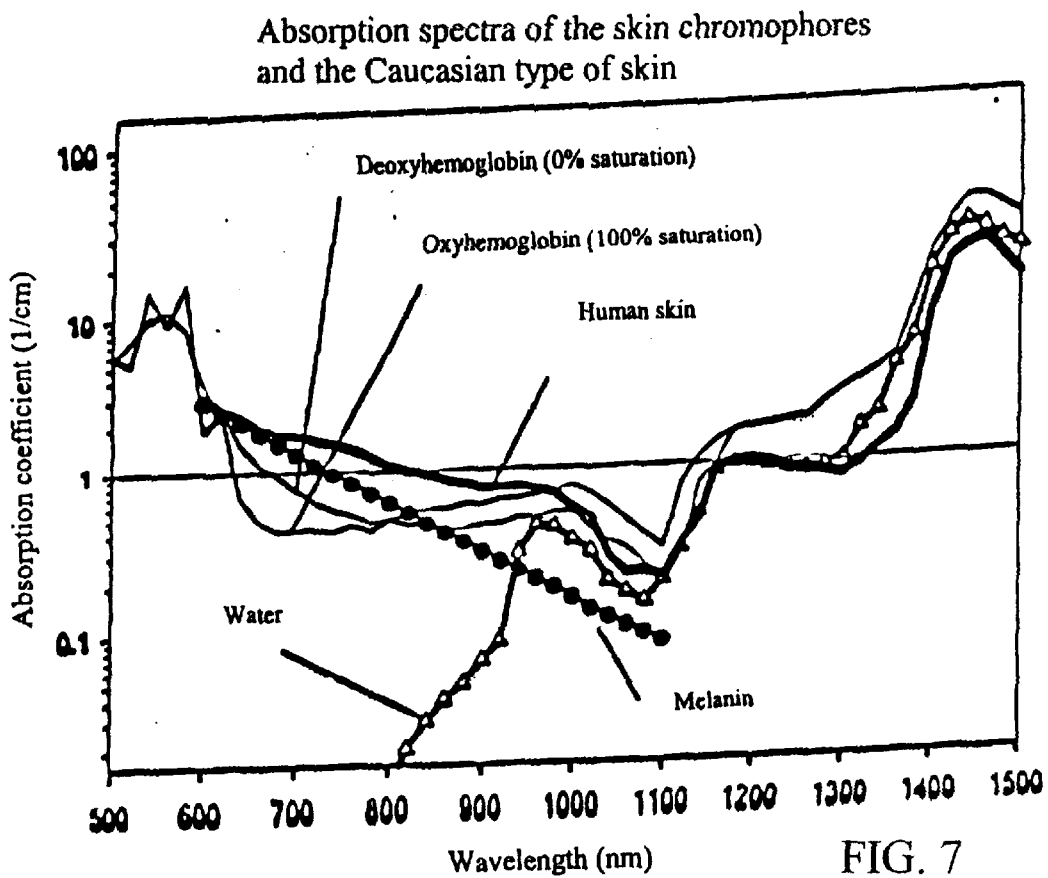

YAG:Er at 2936 nm performs surface wrinkle(superficial) ablation. The effect is based on the very high absorption of YAG:Er laser light in water. This laser works pretty well on small surface wrinkle but does not remove large deep wrinkles because the 2936 nm beam is extremely well absorbed in skin tissue so the penetration is only a few microns. The YAP:Nd laser at 1341 nm will penetrate a few milimeters and provides subsurface wrinkle treatment. Thus, YAP:Nd laser may preferably be used to enhance YAG:Er laser to perform both surface and deep wrinkles treatment. Such a technique is shown in FIG. 5. The approach is similar to those discussed above except in this case the beams are combined in an articulated arm 20 instead of the fiber optic. YAG:Er crystal might be obtained from—Litton Airtron with office in Charlotte, N.C. YAG:Er lasers deck is available from Continuum with office in Santa Clara, Calif., Focus Medical, Bethel, Conn., Fotona, Ljubljana, Slovenia. Articulated arm is available from MedArt Technology, San Diego, Calif.

Simultaneous Application

Both beams should preferably be applied during the the same time interval. The beams may be but do not have to be synchronized. There should not be an significant delay in applying YAG:Er and YAP:Nd laser pulses, since the treated tissue may start to swell very soon after treatment which results in dramatic change in its optical and physiological properties.

Other Embodiments

Other preferred embodiments include other Nd contained laser crystals such as GGG, GSGG, YAG at around 1320 nm or another Er contained crystal YSGG at 2791 nm.

Optical Components

The various optical components needed to fabricate the laser system described above are available from normal optics suppliers and techniques for arranging the components are well known to persons skilled in the laser-optics art. For example the YAP:Nd rods for production of the 1079 nm and 1341 nm beams are available from Crytur, Ltd. with offices in Palackeho175, 51101 Tumov, Czeck Republec and Scientific Material Corp. with offices in Bozeman, Mont. Optics for arranging the resonator cavities are available from CVI Corp. with offices in Albuquerque, N. Mex. Flash lamp pumps for these crystal rods are available from Perkin Elmer with offices in Sunnyvale, Calif. Mirrors 12, 20, 22, and 24 and the optics shown to combine both laser lights are available from CVI Corp.

Preferred Specifications

The power supplies, pump sources and crystal rods should be sized to pulse energies appropriate for the particular treatments planned. In general pulse energies of about 20 J per pulse for the selective beam and about 20 J per pulse for the transmissive beam is recommended. The beam diameters prior to coupling into the optical fiber optic is about 3 mm or more. The beams are normally focused onto the skin surface to produce fluences in the range of about 30 to 90 J per $cm^2$ during the treatment period. Fluencies in excess of 50 J per $cm^2$ could cause severe skin damage. However, as explained above damage can be avoided or minimized with prior, simultaneous or immediately subsequent cooling.

Although the present invention has been described in terms of preferred embodiments the reader should understand many changes and additions could be made without changing the nature of the invention. Therefore, the scope of the invention is to be determined by the appended claims and their legal equivalents.

We claim:

1. A medical-cosmetic laser system comprising:
   A) a first gain medium and a first set of laser optics configured to produce from said first gain medium a first laser beam defining a first absorption coefficient in typical human skin tissue at a first wavelength preferably absorbed in a target tissue, and
   B) a second gain medium and a second set of laser optics configured to produce from said second gain medium a second laser beam at a second wavelength, within the range of about 1000 nm to about 1200 nm, having an absorption coefficient in human skin defining a second absorption coefficient at least 10 times lower than said first absorption coenficient
   C) a combining means for simultaneously combining said first and said second laser beams to produce a combined laser beam and
   D) a means for applying said combined beam simultaneously to tissue for medical or cosmetic treatments; wherein said second laser beam, by penetrating more deeply in tissue than said first laser beam, enhances performances of said first laser beam.

2. A laser beam as in claim 1 wherein said first gain medium and said first set of laser optics is configured as a dye laser capable of producing light at at least one wavelength range in the wavelength of 550 nm to 585 nm.

3. A laser system as in claim 1 wherein said first wavelength is about 2936 nm and said second wavelength is about 1341 nm.

4. A laser system as in claim 1 wherein said first wavelength is about 532 nm and said second wavelength is about 1079 nm.

5. A laser system as in claim 4 wherein said first gain medium comprises a Nd:YAG crystal and a said first set of laser optics comprises a frequency doubling KTP crystal.

6. A laser system as in claim 5 wherein said second gain medium comprises a YAP:Nd crystal and said second set of laser optics are configured to produce 1079 nm laser beams from said YAP:Nd crystal.

7. A method of treatment of tissue comprising the steps of:
   1) simultaneously combining a first laser beam defining a first wavelength having a high first absorption coefficient in a target tissue and defining a first absorption coefficient in said target tissue, with a second laser beam defining a second wavelength having an absorption coefficient in said typical human skin tissue at least 10 times lower than said high first absorption coefficient to produce a combined laser beam and
   2) applying said combined laser beam to tissue for selective destruction of a target tissue; wherein said second laser beam, by penetrating more deeply in said tissue than said first laser beam, enhances performance of said first laser beam.

8. A method as in claim 7 wherein said first laser beam is produced in a dye laser capable of producing light at at least one wavelength rang in the wavelength range of 550 nm to 585 nm.

9. A laser system as in claim 7 wherein said first wavelength is about 2936 nm produced by a YAG:Er laser and said second wavelength is about 1341 nm produced YAP:Nd laser.

10. A method as in claim 7 wherein said first wavelength is about 532 nm and said second wavelength is about 1079 nm.

11. A method as in claim 10 wherein said first laser beam is produced in first laser system comprising a Nd:YAG crystal and a frequency doubling KTP crystal.

12. A method as in claim 11 wherein said second laser beam is produced in a laser comprising a YAP:Nd crystal and said second set of laser optics are configured to produce 1079 nm laser beams from said YAP:Nd crystal.

* * * * *